US008318186B2

(12) United States Patent
Msika et al.

(10) Patent No.: US 8,318,186 B2
(45) Date of Patent: Nov. 27, 2012

(54) USE OF AT LEAST A FATTY ESTER FOR PREPARING A COMPOSITION DESIGNED TO INHIBIT 5-α-REDUCTASE ACTIVITY, IN PHARMACOLOGY, IN PARTICULAR DERMATOLOGY, IN COSMETICS AND AS FOOD ADDITIVE

(75) Inventors: Philippe Msika, Paris (FR); Antoine Piccirilli, Versailles (FR); Jacques Legrand, Neuilly sur Eure (FR)

(73) Assignee: Laboratoires Expanscience, Courbevoie (FR)

( * ) Notice: Subject to any disclaimer, the term of this patent is extended or adjusted under 35 U.S.C. 154(b) by 999 days.

(21) Appl. No.: 10/181,370

(22) PCT Filed: Jan. 18, 2001

(86) PCT No.: PCT/FR01/00168
§ 371 (c)(1),
(2), (4) Date: Aug. 29, 2002

(87) PCT Pub. No.: WO01/52837
PCT Pub. Date: Jul. 26, 2001

(65) Prior Publication Data
US 2003/0129268 A1 Jul. 10, 2003

(30) Foreign Application Priority Data
Jan. 18, 2000 (FR) ..................... 00 00577

(51) Int. Cl.
*A61K 8/02* (2006.01)
*A61K 8/00* (2006.01)
*A61K 9/20* (2006.01)
*C12P 7/64* (2006.01)
(52) U.S. Cl. ........ 424/401; 424/464; 424/70.1; 435/134
(58) Field of Classification Search .................. 424/401, 424/70.1; 514/880; 554/167, 169
See application file for complete search history.

(56) References Cited

U.S. PATENT DOCUMENTS

| 4,664,908 | A | * | 5/1987 | Woods et al. | 424/59 |
| 5,972,345 | A | * | 10/1999 | Chizick et al. | 424/727 |
| 6,127,560 | A | * | 10/2000 | Stidham et al. | 554/167 |
| 6,365,558 | B2 | * | 4/2002 | Lal | 508/491 |
| 6,372,242 | B1 | * | 4/2002 | Gutierrez | 424/411 |
| 6,642,274 | B1 | * | 11/2003 | Neal | 514/573 |

FOREIGN PATENT DOCUMENTS

| DE | 41 34 137 | | 4/1993 |
| EP | 0 039 857 | | 11/1981 |
| EP | 0 415 636 | | 3/1991 |
| EP | 0 897 718 | | 2/1999 |
| JP | 01110610 | A * | 4/1987 |
| JP | 01110610 | | 4/1989 |
| JP | 04288017 | A * | 10/1992 |
| WO | WO 94/01100 | | 1/1994 |
| WO | WO 96/37201 | | 11/1996 |
| WO | WO 98/13330 | | 4/1998 |
| WO | WO 98/52515 | | 11/1998 |
| WO | WO 99/22728 | | 5/1999 |

OTHER PUBLICATIONS

Liang et al. Biochemical Journal. 1992, vol. 285, pp. 557-562.Inhibition of steroid 5 alpha—reductase by specific aliphatic unsaturated fatty acids.*
Database WPI, Section Ch, Week 199216, Derwent Publications Ltd., London, GB, Class D21, AN 1992-126448, XP002149392, & JP 04 066516, Mar. 2, 1992.
Database WPI, Section Ch, Week 199937, Derwent Publications Ltd., London, GB, Class D21, AN 1992-187477, XP002149393, & JP 02 066516, Mar. 2, 1992.
Liang et al., "Inhibition of Steroid 5-Alpha-Reductase by Specific Aliphatic Fatty Acids," Clinical Research, US, Thorofare, NJ, vol. 39, No. 3, 1991, p. 720A, XP000600261.
Liang et al., "Inhibition of Steroid 5-Alpha-Reductase by Specific Aliphatic Unsaturated Fatty Acids," Biochemical Journal, GB, Portland Press, London, vol. 285, 1992, pp. 557-562, XP000600136.
Niederpruem et al, "Inhibition of Steroid 5-Alpha-Reductase Activity by Aliphatic Fatty Acids. Candidates for Chemoprevention of Prostate Cancer," Annals of the New York Academy of Sciences, vol. 768, 1995, pp. 227-230, XP000949291.
Chen, et al., "The 5α-reductase system and its inhibitors," *Dermatology*, vol. 193(3), pp. 177-184, 1996.
Mercurio et al., "Androgen physiology and the cutaneous pilosebaceous unit," *J. Gend. Specif. Med.*, vol. 3(4), pp. 59-64, 2000.
Spinucci, et al., "[Finasteride: a new drug for the treatment of male hirsutism and androgenetic alopecia?]," *Clin. Ter.*, vol. 147(6), pp. 305-315, 1996.

* cited by examiner

*Primary Examiner* — Lakshmi Channavajjala
(74) *Attorney, Agent, or Firm* — Foley & Lardner LLP

(57) ABSTRACT

The invention concerns the use of at least a fatty ester for preparing a composition designed to inhibit 5α-reductase activity. Said use produces a remarkable inhibiting effect of 5α-reductase thereby providing a novel response for treating dermatological pathologies and/or disorders related to congenital or acquired exaggeration of 5α-reductase activity, in particular for treating prostatic hypertrophy, prostatic adenoma, acne, hyperseborrhea, alopecia and hirsutism. The invention also concerns cosmetic treatment methods, in particular for greasy skin, and the use of said fatty esters as additives in a food product for human and/or animal consumption.

21 Claims, No Drawings

USE OF AT LEAST A FATTY ESTER FOR PREPARING A COMPOSITION DESIGNED TO INHIBIT 5-α-REDUCTASE ACTIVITY, IN PHARMACOLOGY, IN PARTICULAR DERMATOLOGY, IN COSMETICS AND AS FOOD ADDITIVE

The present invention relates to the use of at least one fatty ester for preparing a composition designed to inhibit 5α-reductase activity, in particular for treating prostatic hypertrophy, prostatic adenoma, acne, hyperseborrhea, alopecia and hirsutism. The invention also relates to methods for cosmetic treatment, in particular of greasy skin, and the use of the fatty esters described as additives in a food product for human and/or animal consumption.

5α-Reductase is a NADPH-dependent microsomial enzyme which exists in the form of two isoenzymes synthesized from two different genes. The 5α-reductase type 1 isoenzyme is essentially found in the liver and the skin, more particularly in the sebaceous glands of nongenital skin and of the scalp, and appears at puberty. The type 2 isoenzyme is predominant in the prostate and in the skin of differentiated sexual areas: genital region, beard, and plays a role in sexual differentiation. The distribution of the 5α-reductase types 1 and 2 isoenzymes in the skin and cutaneous annexes in humans may be illustrated by the following table.

TABLE 1

Distribution of the 5α-reductase types 1 and 2 isoenzymes in the skin and cutaneous annexes in humans

| | | H5-r1 | H5-r2 |
|---|---|---|---|
| EPIDERMIS | Basal layer | ++ | + |
| | Spinous layer | + | ++ |
| | Granular layer | + | − |
| | Horny layer | − | − |
| DERMIS | Fibroblasts | ++ | − |
| SEBACEOUS GLANDS | Basal cells | ++ | + |
| | Glandular cells | ++ | − |
| ECCRINE SWEAT GLANDS | Excretory canal | − | − |
| | Secretary cells | ++ | − |
| | Myoepithelial cells | ++ | + |
| HAIR FOLLICLE | Dermal papilla | + | +? |
| | Cells of the matrix | ++ | + |
| | Inner epithelial sheath | ± | +++ |
| | Outer epithelial sheath | ++ | − |
| | Arrector muscle | + | − |

A number of pathologies exist for which a congenital or acquired exaggeration of the 5α-reductase activity is completely or predominantly responsible for the disorders observed.

For example, in humans, this 5α-reductase enzyme, mainly located in the genital tissues and in the skin, catalyzes the hydroxylation of testosterone to 5α-reductase dihydrotestosterone (DHT). However, since DHT is an androgen which is much more active than testosterone (about twice as much), the effects of the latter are amplified in tissues where DHT is produced. An excessively high activity of 5α-reductase thus causes excessively high levels of androgen in the form of DHT in the prostate, hence an overstimulation of the latter resulting in an undesirable growth which can lead to the pathology of prostatic hypertrophy, or even to prostatic adenoma, most often requiring a surgical operation.

Other pathologies, of the dermatological type, may be observed in men or women as resulting from an overactivity of 5α-reductase, namely in particular acne, hirsutism or alopecia.

In the skin, the 5α-reductase activity is higher in the sebaceous gland than in other structures. Moreover, the seborrheic glands show a higher 5α-reductase activity than those of other skin areas. Consequently, the level of physiological sebaceous secretion appears to be closely linked to the activity of this enzyme.

In acne sufferers, a hyperactivity of 5α-reductase exists. More than an increase in the serum androgen levels it is an increase in the precursors of DHT, main factor for the sebaceous function, which participates in acne. Greasy or seborrheic skin, apart from its unsightly appearance, constitutes a ground on which complications may occur. It affects the regions where the sebaceous glands are numerous and mainly results from an androgenic overstimulation of sebaceous production by these specific glands. Hyperseborrhea participates in the onset of lesions caused by acne vulgaris.

In the scalp, the 5α-reductase type 1 isoenzyme is found in the sebaceous glands, as well as in the hair follicle. The 5α-reductase type 2 isoenzyme is predominantly located in the inner epithelial sheath, and in the dermal papilla of the hair. However, this latter location remains to be specified.

Androgenic alopecia, whose physiopathogeny is very similar to that of acne, is the most frequent of alopecias and undoubtedly that in which the demand for therapy is the greatest. 5α-Reductase appears to play a key role in this pathology. Indeed, men affected by a genetic deficiency in 5α-reductase type 2 isoenzyme do not develop androgenic alopecia.

Taking into account the preceding text, research has been directed toward the development of 5α-reductase inhibitors. Some steroids such as progesterone have been tested in this context, but its rapid metabolization makes it ineffective in vivo. To be active, the 5α-reductase inhibitor should be sufficiently stable in order to block the activity of the enzyme in vitro. Finasteride, a competitive steroidal inhibitor, fulfils this condition, but it is more active on the type 2 isoenzyme than on the type 1 isoenzyme and these two isoenzymes have only 50% homology on their amino acid sequence. It is therefore especially in benign hyperplasia of the prostate that finasteride has already been tested.

Moreover, *Serenoa Repens* extract is also known as reference as a 5α-reductase inhibitor, the *Serenoa Repens* extract having the advantage, compared with finasteride, of a natural origin as a plant extract, allowing better comparison for products tested which are also of natural origin. *Serenoa Repens*, also known by the name *Sabal serrulatum*, is a small palm tree which is found in the United States (Florida), in North Africa and in Spain.

It has now been found, quite surprisingly and unexpectedly, that the use of certain compounds, fatty esters, makes it possible to obtain a remarkable 5α-reductase activity inhibiting effect, thus providing in particular a novel response for the treatment of the dermatological pathologies and/or disorders mentioned above.

The present invention thus relates to the use of at least one fatty ester for preparing a composition designed to inhibit 5α-reductase activity.

In particular, the use according to the invention is characterized in that the composition is designed to inhibit the 5α-reductase type 1 isoenzyme and/or type 2 isoenzyme.

The expression "fatty ester" is understood to mean according to the invention, in accordance with the general knowledge of persons skilled in the art, a molecule comprising at least one ester functional group and at least one "fatty" hydrocarbon chain, that is to say a linear hydrocarbon chain of at least 7 carbon atoms.

The fatty ester which can be used according to the invention comprises at least one ester functional group and at least one fatty chain, the ester functional group comprising a $C_1$-$C_{30}$ alkoxy group whose hydrocarbon chain is linear or branched, optionally substituted with one to 3 hydroxyl groups, and the fatty chain being a linear $C_7$-$C_{30}$ hydrocarbon chain containing between 0 and 2 ethylenic unsaturations, optionally substituted with 1 to 3 hydroxyl groups and/or 1 to 3 ester functional groups (of course in addition to the principal ester functional group).

In particular, the ester functional group may comprise a $C_1$-$C_{22}$, and more particularly $C_1$-$C_{18}$, alkoxy group, as in the case of a monoglyceride (glycerol monoester) and/or may be a branched chain such as, for example, an isopropyl or isobutyl.

The fatty chain is preferably an ethylenically unsaturated linear $C_7$-$C_{30}$ hydrocarbon chain comprising 1 or 2 conjugated or nonconjugated ethylenic unsaturations, as for example in the case of methyl linoleate.

The fatty chain may advantageously comprise in particular from 1 to 22, and more particularly from 1 to 18 carbon atoms.

The preparation of the fatty esters which can be used according to the invention falls within the methods known to persons skilled in the art. The methods for preparing esters not cited in the text which follows but which form part of the general knowledge of persons skilled in the art may therefore also be used.

Of course, there may be mentioned, firstly, the esterification of a fatty acid whose fatty chain corresponds to that of the desired fatty ester, with the alcohol whose hydrocarbon part corresponds to that of the alkoxy group of the desired fatty ester.

The formation of the esters from the carboxy acids and the alcohols may be carried out either directly, or by converting the acid to more reactive derivatives, or by activating the alcohol for a condensation with the carboxylate.

The direct esterification of a carboxylic acid with an alcohol is a balanced reaction, catalyzed by strong protonic acids. The reaction is carried out with a large excess of alcohol in a solvent which forms an azeotrope removed by distillation. The methyl esters may be obtained from solutions of hydrochloric methanol at 5% or sulfuric methanol at 1-3%. It is possible to use Lewis acids as catalysts. The specific case of direct esterification between a fatty acid and glycerol in the presence of homogeneous or heterogeneous acid catalysts may also be mentioned.

The activation of the carbonyl consists in converting the hydroxyl to a better leaving group. The acid chlorides are the derivatives most frequently used. The use of acid anhydrides may also be mentioned.

The activation of the alcohol consists in making it more reactive toward a nucleophilic attack by the carboxylate ion. The diazomethane is a very reactive source of methyl after deprotonation of the acid.

Finally, the esterification of the carboxylic acids may also be carried out by the enzymatic route. Lipases catalyze the esterification. These lipases are obtained from microorganisms of the genera *Aspergillus, Candida, Geotrichum, Mucor, Penicillium*.

Moreover, the fatty esters which can be used according to the invention may be prepared by transesterification which is a reaction between an ester and an alcohol leading to a different ester. Three types of reaction are grouped under the term transesterification:

alcoholysis which is a reaction between an ester and an alcohol;

acidolysis which is a reaction between an ester and a carboxylic acid (or an acid anhydride);

interesterification which is an exchange reaction between two esters, of the nonalkoxy groups.

The transesterification is advantageously catalyzed by homogeneous or heterogeneous catalysis.

Numerous homogeneous (acid or base) catalysts are described in the literature. The acid catalysts may be strong inorganic acids such as sulfuric, sulfonic, phosphoric or hypochloric acid, but also organic acids such as para-toluenesulfonic or methanesulfonic acid. The base catalysts commonly used in transesterification are conventional bases such as hydroxides (sodium hydroxides or potassium hydroxides), carbonates ($K_2CO_3$, $Na_2CO_3$) and alcoholates ($NaOCH_3$, NaOEt).

In heterogeneous catalysis for transesterification, it is possible to use Lewis acids, but they are generally not very active. It has also been shown that tributyltin alcoholate ($Bu_3SnOR$) could catalyze the transesterification reaction between an alcohol and an ester at 120° C. for an alcohol/ester molar ratio of 10. Titanium alcoholates ($Ti(OR)_4$) have been used for a long time in industry as active transesterification catalysts. However, it is necessary to hydrolyze them and to filter them at the end of the reaction in order to remove them from the reaction medium. In particular, supported titanates have proved active during methanolysis of the soybean oil.

Among the other catalysts which can be used for a heterogeneous catalysis of transesterification, there may also be mentioned guanidines, lanthanides, enzymes such as lipases like *Pseudomonas* sp or *Mercor Miehei*, alkaline-earth metal oxides, magnesium oxide and finally supported catalysts such as basic centers (calcium oxide) supported on varied oxides (magnesium oxide, alumina, silica and the like).

Heterogeneous catalysis has the advantages, compared with homogeneous catalysis, of using catalysts which can be more easily separated from the reaction medium and of causing fewer problems of corrosion and of side reactions.

The starting materials for the esterification reactions described above may be of synthetic or natural origin, in particular of animal or plant origin.

Fatty substances of plant or animal origin are preferred as starting materials which provide the fatty chain of the fatty esters used according to the invention.

It is thus possible to carry out an esterification as described above of a fatty acid, in particular of plant origin, with an alcohol.

Among the fatty acids which can be used for these esterification reactions, there may be mentioned in particular the fatty acids obtained from fatty acid soaps which are by-products of the saponification of a vegetable oil. This indeed involves a very advantageous enhancement of the value of these by-products of the preparation of the unsaponifiable components of vegetable oil.

Among the vegetable oils which may be used, there may be mentioned in particular sunflower, palm, palm kernel, coconut, grape-seed, black mustard, poppy-seed, karite butter, sweet almond, soybean, avocado, lupine, peanut, cottonseed, sesame, olive, corn, cocoa, castor, ben, linseed, colza, annatto, wheat germ, safflower, nut, hazelnut and rapeseed oil. Avocado oil and soybean oil are particularly preferred.

The saponification of the oil, in particular of avocado (or soybean) oil is an essential step of the method for producing unsaponifiable components. This step, which is carried out in the presence of aqueous potassium hydroxide and ethanol, is a basic hydrolysis of the oil (triglycerides) leading to the formation of potassium soaps and glycerol:

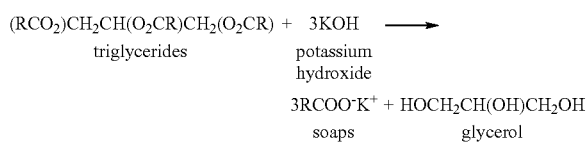

$$3RCOO^-K^+ + HOCH_2CH(OH)CH_2OH$$
soaps        glycerol

The unsaponifiable component, in emulsion in the aqueous-alcoholic phase ("soapy" phase), is then extracted with dichloroethane (DCE) according to a liquid-liquid extraction method. After extraction, the aqueous-alcoholic phase, freed of the unsaponifiable fraction, is a mixture consisting essentially of soaps, ethanol, water, glycerol, DCE and fraction I. Fraction I is one of the components of the unsaponifiable component of avocado. It constitutes substrates having a fatty alkyl chain (radical R) and hydroxyl functional groups:

$$RCH_2-CH(OH)CH_2CH(OH)CH_2OH$$

These hydroxylated compounds are partially soluble in the aqueous-alcoholic phase.

After the liquid-liquid extraction step, the "soapy" phase is acidified with sulfuric acid. The soaps are then converted to fatty acids (reaction 1 below). The mixture obtained is then distilled so as to remove the ethanol and the traces of DCE. The fatty acids and the water are finally separated by decantation.

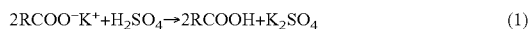

$$2RCOO^-K^+ + H_2SO_4 \rightarrow 2RCOOH + K_2SO_4 \quad (1)$$

These crude avocado fatty acids are finally purified, for example on a silica column (eluent hexane and then hexane-diethyl ether 95:9) or by molecular distillation and may thus constitute the raw material used during the synthesis of the avocado fatty esters, in particular of the avocado methyl esters. The fatty acids of soybean or of another vegetable oil such as those cited above may be obtained according to the same route of synthesis.

Thus, according to a particular embodiment, the fatty ester used according to the invention is obtained by esterification of at least one fatty acid of at least one vegetable oil, it being understood that the expression "vegetable oil fatty acid" covers according to the invention the fatty acids originally present in said vegetable oil and the fatty acids which may be obtained by treating the soapy phase after saponification of said vegetable oil, as described above.

The triglycerides present in the fatty substances of plant origin (in particular vegetable oils) or of animal origin (in particular fish oils) may also represent a non-negligible source of fatty esters which can be used according to the invention, via a transesterification using means known to persons skilled in the art as described above.

Thus, according to another particular embodiment, the fatty ester used according to the invention is obtained by transesterification of the triglycerides of at least one vegetable oil, as described above.

Regardless of the route of synthesis selected, a fatty ester is advantageously used according to the invention which is chosen from the group consisting of fatty esters of avocado and soybean oil and mixtures thereof.

More particularly, the fatty ester consists of alkyl esters of avocado oil, alkyl esters of soybean oil and a mixture thereof. The expression "alkyl esters of avocado oil" (respectively "alkyl esters of soybean oil") is understood to mean according to the invention a mixture of fatty esters obtained by esterification of fatty acids of avocado oil (respectively soybean oil), fatty acids which have been obtained by treating the soapy phase after saponification of the avocado oil (respectively soybean oil) and then subjected to an esterification with at least one alcohol or a mixture of alcohols, whose alkyl group determines the "alkyl" part of these alkyl esters. For example, the use of butanol thus makes it possible to obtain "butyl" esters. Preferably, an alcohol is used which has from 1 to 6 carbon atoms, whose alkyl group is linear or branched, such as for example isopropanol. It is of course understood that this definition covers the use, for such an esterification, of a mixture of alcohols as already mentioned above, for example of a mixture of butanol and methanol. Preferably still, such an esterification is carried out with a catalytic mixture, in particular a $BF_3$/ethyl ether mixture.

More particularly, the fatty ester consists of methyl esters of avocado oil, methyl esters of soybean oil or a mixture thereof. The expression "methyl esters of avocado oil" (respectively "methyl esters of soybean oil") is understood to mean according to the invention a mixture of fatty esters obtained by esterification of fatty acids of avocado oil (respectively soybean oil), the fatty acids having been obtained by treating the soapy phase after saponification of the avocado oil (respectively soybean oil) and then subjected to esterification with methanol, preferably with a catalytic mixture, in particular a $BF_3$/ethyl ether mixture.

Still more particularly, the fatty ester consists of butyl esters of avocado oil, butyl esters of soybean oil or a mixture thereof. The expression "butyl esters of avocado oil" (respectively "butyl esters of soybean oil") therefore is understood to mean according to the invention a mixture of fatty esters obtained by esterification of fatty acids of avocado oil (respectively soybean oil), the fatty acids having been obtained by treating the soapy phase after saponification of the avocado oil (respectively soybean oil) and then subjected to esterification with butanol, preferably with a catalytic mixture, in particular a $BF_3$/ethyl ether mixture. The butyl esters of avocado and soybean oils are characterized as follows:

Butyl Esters of Avocado Oil

| | |
|---|---|
| Contents of butyl esters | 95% min. |
| Acid value | <5 |
| Residual unsaponifiable component | <0.5 wt % |
| Distribution of fatty acids: | |
| Palmitic acid C16 | 12 to 25% |
| Palmitoleic acid C16' | 3 to 10% |
| Stearic acid C18 | traces |
| Oleic acid C18' | 45 to 75% |
| Linoleic acid | 6 to 18% |
| Linolenic acid C18' | <5% |

Butyl Esters of Soybean Oil

| | |
|---|---|
| Content of butyl esters | 95% min. |
| Acid value | <5 |
| Residual unsaponifiable component | <0.5 wt % |
| Distribution of fatty acids: | |
| Myristic acid C14 | <0.2% |
| Palmitic acid C16 | 9 to 13% |
| Palmitoleic acid C16' | <0.3% |
| Stearic acid C18 | 3 to 5% |
| Oleic acid C18' | 17 to 30% |
| Linoleic acid C18" | 48 to 58% |
| Linolenic acid C18' " | 5 to 11% |
| Arachidic acid C20 | <1% |
| Eicosenoic acid C20' | <1% |
| Behenic acid C22 | <1% |

According to another particularly preferred embodiment of the present invention, at least one fatty ester is used which is chosen from the group consisting of methyl oleate, methyl linoleate, methyl stearate, methyl laurate, methyl undecylenate, butyl oleate, oleyl oleate, methyl ricinoleate, methyl palmitate, methyl palmitoelate, and mixtures thereof.

According to the invention, the fatty ester as described above is used in a proportion of between about 0.001 and about 100% by weight (use in pure form, for example as an emollient), preferably between about 0.01 and about 70% by weight, and still more particularly between about 0.1 and 10% by weight, relative to the total weight of the composition.

The composition prepared by the use according to the invention may, in addition, comprise a pharmaceutically, dermatologically or cosmetically acceptable excipient. It is possible to use any excipient suitable for galenic forms known to persons skilled in the art for administration by the topical, oral, enteral or parenteral, in particular rectal, route.

In particular, this excipient may be suitable for the production of a composition in the form of an oily solution, of a water-in-oil emulsion, an oil-in-water emulsion, a microemulsion, an oily gel, an anhydrous gel, a cream, a dispersion of vesicles, of microcapsules or of microparticles, or alternatively of hard gelatin capsules or of plant or soft gelatin capsules.

Preferably, an excipient is used which is suitable for administration by the external topical route or by the rectal route.

The advantageous effect of inhibition of the 5α-reductase activity provided by the use according to the invention makes it possible to design the composition thus prepared for therapeutic, in particular dermatological, and cosmetic treatments.

Thus, the use according to the invention is characterized in that the composition is designed for treating skin pathologies and/or disorders related to congenital or acquired exaggeration of 5α-reductase activity.

In particular, the use according to the invention is characterized in that the composition is designed for treating prostatic hypertrophy.

In addition, the use according to the invention is characterized in that the composition is designed for treating prostatic adenoma.

The use of an excipient suitable for administration by the rectal route as described above may be particularly envisaged for these treatments of prostatic hypertrophy and/or adenoma.

The use according to the invention is also characterized in that the composition is designed for treating acne.

The use according to the invention is also characterized in that the composition is designed for treating hyperseborrhea.

Finally, the use according to the invention is also characterized in that the composition is designed for treating alopecia.

The use according to the invention is also characterized in that the composition is designed for treating hirsutism.

The subject of the present invention is also a method for the cosmetic treatment of greasy skin, characterized in that a cosmetic composition containing at least one fatty ester as described above is applied to the skin.

The subject of the invention is moreover a method for the cosmetic treatment of hair loss, characterized in that a cosmetic composition containing at least one fatty ester as described above is applied to the scalp.

Finally, the subject of the invention is also a method for the cosmetic treatment of excess pilosity, characterized in that a cosmetic composition containing at least one fatty ester as described above is applied to the regions of the skin exhibiting excess pilosity.

In fact, unlike hormonal medical treatments, the latter two methods of cosmetic treatment make it possible to improve the appearance by visibly reducing the unsightly phenomena of hair loss related to alopecia and the phenomena of excess pilosity related to hirsutism.

According to a preferred embodiment of these methods of cosmetic treatments, the fatty ester is present in the composition in a proportion of between about 0.001 and about 100% by weight (use in pure form, without excipient, for example as an emollient), preferably between about 0.01 and about 70% by weight, and still more particularly between about 0.1 and 10% by weight, relative to the total weight of the composition.

Advantageously, the cosmetic composition applied according to the cosmetic method of the invention contains, in addition, at least one cosmetically acceptable excipient as described above.

Finally, the subject of the invention is furthermore the use of at least one fatty ester, as described above, as additive in a food product for human and/animal consumption. This food use is preferably characterized in that the fatty ester is present in the food in a proportion of between about 0.001 and about 100% by weight, preferably between about 0.01 and about 70% by weight, and still more particularly between about 0.1 and 10% by weight, relative to the total weight of the food.

The following examples are intended to illustrate the present invention and should not in any case be interpreted as being capable of limiting the scope thereof.

Unless otherwise stated, the percentages indicated in the following examples are percentages by weight.

EXAMPLE 1

Preparation of Methyl Esters of Avocado Oil and of Soybean Oil

Methyl esters of avocado oil and of soybean oil are prepared according to the following procedure:

1. Production of Purified Avocado and Soybean Fatty Acids

The saponification of avocado (or soybean) oil is an essential step of the method for producing unsaponifiable components. This step, carried out in the presence of aqueous potassium hydroxide and ethanol, is a basic hydrolysis of the oil (triglycerides) leading to the formation of potassium soaps and of glycerol:

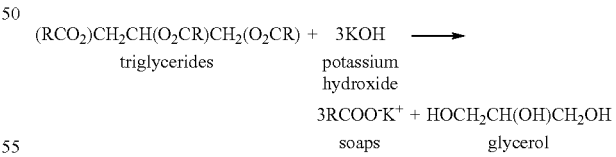

The unsaponifiable component, in emulsion in the aqueous-alcoholic phase ("soapy" phase), is then extracted with dichloroethane (DCE) according to a liquid-liquid extraction method. After extraction, the aqueous-alcoholic phase, freed of the unsaponifiable fraction, is a mixture consisting essentially of soaps, ethanol, water, glycerol, DCE and fraction I. Fraction I is one of the components of the unsaponifiable component of avocado. It consists of substrates having a fatty alkyl chain (radical R) and hydroxyl functional groups:

These hydroxylated compounds are partially soluble in the aqueous-alcoholic phase.

After the liquid-liquid extraction step, the "soapy" phase is acidified with sulfuric acid. The soaps are then converted to fatty acids (reaction 1). The mixture obtained is then distilled so as to remove the ethanol and the traces of DCE. The fatty acids and the water are finally separated by decantation.

$$2RCOO^-K^+ + H_2SO_4 \rightarrow 2RCOOH + K_2SO_4 \quad (1)$$

These crude avocado fatty acids are finally purified on a silica column (eluent hexane and then hexane-diethyl ether 95:5) and thereby constitute the raw material used during the synthesis of the avocado methyl esters.

The soybean fatty acids are obtained according to the same route of synthesis.

2. Preparation of the Methyl Esters of Avocado Oil and of Soybean Oil

The methyl esters of avocado are obtained according to the following procedure:

250 ml of methanol, 500 g of avocado fatty acids and 12.5 ml of a BF3/ethyl ether mixture are mixed in a three-necked round-bottomed flask equipped with a condenser and magnetic stirring. The reaction mixture is then heated under reflux for 1 hour.

The methyl esters thus obtained are dried under vacuum in a rotary evaporator and then finally purified by molecular distillation, at 120° C. under a vacuum of 4 μm of mercury and with a distillation rate of 90%.

The soybean fatty esters are obtained according to the same route of synthesis.

It is also possible, for example, to obtain butyl esters of avocado oil and of soybean oil respectively according to the same route of synthesis except that methanol is replaced with butanol (see example 6 of composition below).

3. Analysis of the Products Obtained 3.1 Composition of the Purified Avocado Fatty Acids

TABLE 2

| | |
|---|---|
| Content of fatty acids | 96.2% |
| Residual unsaponifiable component | 3.8% |
| Distribution of fatty acids: | |
| Myristic acid C14:0 | 0.08% |
| Palmitic acid C16:0 | 22.7% |
| Palmitoleic acid C16:1 | 9.9% |
| Stearic acid C18:0 | 0.6% |
| Oleic acid C18:1 | 50.3% |
| Linoleic acid C18:2 | 11.8% |
| Linolenic acid C18:3 | 0.9% |

3.2 Composition of the Avocado Methyl Esters

TABLE 3

| | |
|---|---|
| Methyl esters of fatty acids | 86.0 |
| Residual unsaponifiable component | 2.1 |
| Components not determined | 11.9 |
| Distribution of fatty acids: | |
| Palmitic acid C16:0 | 25.1% |
| Palmitoleic acid C16:1 | 8.4% |
| Stearic acid C18:0 | 0.6% |
| Oleic acid C18:1 | 55.8% |
| Linoleic acid C18:2 | 9.1% |
| Linolenic acid C18:3 | 0.4% |

3.3 Composition of the Soybean Methyl Esters

TABLE 4

| | |
|---|---|
| Methyl esters of fatty acids | 97.8 |
| Residual unsaponifiable component | — |
| Components not determined | 2.2 |
| Distribution of fatty acids: | |
| Palmitic acid C16:0 | 20.4% |
| Palmitoleic acid C16:1 | 0.2% |
| Stearic acid C18:0 | 2.9% |
| Oleic acid C18:1 | 20.9% |
| Linoleic acid C18:2 | 49.8% |
| Linolenic acid C18:3 | 2.8% |

EXAMPLE 2

Evaluation of the Inhibitory Activity on the 5α-Reductase Activity by Measuring the Quantity of 5-Dihydrotestosterone Formed From Testosterone by DU145 Cells 1. Materials and Methods 1.1 Materials The prostatic cells DU145 are derived from a tumor line obtained from a prostate carcinoma (ATCC No. HTB 81). The MEM medium (ref. 0410265), the glutamine and the gentamycin are from Gibco. The fetal calf serum (FCS) is from DAP and is used decomplementized (45 mm at 56° C.). The plastics serving for the culture (dishes and plates) are from Costar. The testosterone is from Sigma.

1.2 Method 1.2.1 Preparation of the Product Ranges

A stock solution in ethanol at 10 mg/ml is prepared from each of the products tested.

The concentration range used for the experiments is the following: 0, 5, 10, 50, 100 and 500 micrograms/ml. (Dilution performed in the culture medium).

The volume of extract added per well being 20 microliters/well, the solutions to be prepared are concentrated 50×.

Preparation of Testosterone

A stock solution of testosterone at 10 mM is prepared in ethanol. At the time of its use, this solution is diluted 1:1 000 in the culture medium and 10 microliters are added per well.

1.2.2 Experiment of Inhibition of the 5α-Reductase of DU145 Cells

The prostatic cells DU145 are cultured at 37° C., 5% $Co_2$ in an MEM medium containing glutamine (2 mM), gentamycin (50 micrograms/ml) and 10% FCS. Their subculture rate is 1:10.

Before starting the experiment, the cells are placed in culture in 6-well plates at the rate of $2 \times 10^5$ DU145 cells per well/1 ml of medium containing only 1% FCS. The cells are maintained for 3 days at 37° C., 5% $CO_2$. On the day of the experiment, the culture medium contained in the wells is removed and replaced with fresh medium containing 1% FCS. The testosterone (0.1 micromolar final) as well as the extracts at the different concentrations are added to the medium at the rate of 10 to 20 microliters/well respectively. (The "control" wells correspond to cells incubated in the presence of testosterone and of one equivalent ethanol. This makes it possible to substract the effect of the solvent on the cultures and to determine the percentage of DHT formed in the absence of inhibitor). The cells are then incubated at 37° C., 5% $CO_2$. After 3 hours, the culture supernatants are collected and frozen at −80° C. until assayed.

Measurement of the Quantity of DHT Formed
Principle: extraction of the lipophilic products with ether, concentration of the samples with respect to DHT by affinity chromatography and radioimmunological assay.

Preparation of the Samples
  After having vortexed the samples, introduce the samples into "SEPEX" flasks
  Add to each tube 0.1 ml of radioactive solution "3H-Rdt" (for evaluation of the extraction yield). Close the flasks, vortex them one by one.
  Allow to stand for 30 min at room temperature. Then vortex each flask again.
  Add to each flask: 5 ml of diethyl ether.
  Close the flasks and manually shake them vigorously. Allow to settle for a few minutes.
  Freeze the aqueous phases at −30° C., for at least 1 hour.
  Collect the ethereal phase in a corresponding 5 ml borosilicate test tube.
  Completely evaporate the ethereal phase using the evaporator+water bath system at 37° C.

Separation of the DHT
  Preparation of the columns: Prepare the columns in 5 ml glass culture pipettes with 10 cm of chromatolithe A.
  Rinsing of the columns: 3 ml of combitips pure isooctane (3 times), allowing it to flow by mere gravity.
  Elution of the dry ethereal extracts
    Each dry extract is taken up in 1 ml of pure isooctane, vortex vigorously.
    Wait for 15 min at room temperature. Vortex again.
    When the 3 ml of isooctane (washing of the columns) have been eluted, pour the dry ethereal extracts taken up in isooctane over the column. Allow to elute.
    Rinse each "dry extract" tube with 1 ml of combitips pure isooctane, vortex vigorously. Wait for 15 min at room temperature. Vortex again and pour into the column as above.
    Wash with 4 ml of pure isooctane.
  Collect the DHT
    Prepare the elution solvent (mixture containing 6% isooctane/ethyl acetate: 94/6 (v-v))
    Elute with 6 ml (pipette) of this mixture.
    Collect the DHT eluate in the 5 ml borosilicate test tubes identified.
  Treatment of the DHT eluate: Evaporate the eluate solvent using the evaporator-water bath system (37° C.)

RIA Assay
  Distribution protocol: Take up the samples with 0.5 ml of RC buffer, the Blank with 1 ml of Rcet buffer, the Controls with 0.5 ml of RC buffer. Place in an oven at 37° C. for 15 min Shake the tubes again on coming out of the oven (1 min).
  In the identified 5 ml glass hemolysis tubes, place in order:
  Buffer: Total Activity (TA): 0.7 ml of RC buffer, Nonspecific Activity (N): 0.2 ml of RC buffer, Range: only point 0 of the range (note BO) contains 0.1 ml of RC buffer, Standard solution (1 000 to 7.8 pg/tube): 0.1 ml of the respective standard solution.
  0.1 ml of dry extract taken up in the buffer
  Then, distribute the antiserum: 0.1 ml in all the tubes except TA and N.
  Then, distribute the assay solution "3HD": 0.1 ml in all the tubes.
  Vortex and cover with parafilm.
  Incubation at 4° C. for 1 h 30 min minimum (24 h maximum).
  Preparation of the charcoal-dextran: place the charcoal-dextran suspension in a beaker, then in an ice-cold water bath at 4° C., for at least 1 h 30 min.

DHT purification yield
  In 6 small scintillation flasks (3 per series) deposit: 0.4 ml of RC buffer+0.1 ml of "3H-Rdt" solution (flask from the first day in the refrigerator). Blanks: place 0.5 ml of reconstituted dry extract for the blank. Samples and controls: place 0.25 ml of RC buffer+0.25 ml of extract.
  Add 5 ml of scintillation liquid to all the flasks.

Separation of the Free Dht from that Bound to the Antibody
  Place the charcoal-dextran suspension under magnetic stirring in a basin of ice-cold water.
  Add 0.5 ml of charcoal-dextran to all the tubes except TA over 2 min maximum.
  Vortex, return the tubes to the ice-cold water. Wait for exactly 10 min. Centrifuge at 4° C., 3 400 rpm, for 11 min
  Pipette 0.5 ml of each supernatant (including TA) into a small counting flask
  Add 5 ml of scintillation liquid. Stir, allow to equilibrate for 30 min at room temperature.
  Count for 2 min with the β counter (Beckman, LS 6000 SE).

2. Results 2.1 Evaluation of the Conversion of Testosterone to 5-Dihydrotestosterone by the DU 145 Cells—Determination of the IC 50 Values

TABLE 5

| Product tested | IC 50 (µg/ml) |
| --- | --- |
| Fatty acids of avocado oil (1) | 510 |
| Methyl esters of avocado oil (1) | 13 |
| Methyl esters of soybean oil (1) | 304 |
| Methyl oleate (2) | 386 |
| *Serenoa repens* | 60 |

(1) obtained as described in example 1
(2) commercial product (Sigma, 99% purity)

3. Conclusions

In general, the methyl esters of fatty acids exhibit a 5α-reductase inhibitory activity.

Among them, the methyl esters of avocado oil constitute the most active product. They are 5 to 6 times more active than the *Serenoa repens* extract, a recognized 5α-reductase inhibitor.

The methyl esters of avocado oil are more active than their soybean oil homologues.

The methyl esters of avocado exhibit a 5-alpha-reductase inhibitory activity unlike their precursors, the fatty acids of avocado, which exhibit a markedly lower activity on this enzyme.

Finally, methyl oleate, predominant constituent of the methyl esters of avocado (50%), tested alone, proves markedly less active than the methyl esters of avocado.

EXAMPLE 3

Evaluation in vitro of the 5-αReductase Activity on the Conversion of Testosterone to 5α-Dihydrotestosterone in Cultures of Normal Human Dermal Fibroblasts.

Abbreviations Used in the Following Examples:

| | |
| --- | --- |
| $^3$H | tritium |
| TLC | thin-layer chromatography |
| Ci | Curie |
| DMSO | dimethyl sulfoxide |
| M199 | name given to a standard culture medium |

-continued

| | |
|---|---|
| FCM | fibroblast culture medium |
| MEM | name given to the culture medium Minimum Essential Medium |
| FIM | fibroblast incubation medium |
| Rf | relative retardation factor |
| FCS | fetal calf serum |
| 5α-DHT | 5α-dihydrotestosterone |

It is proposed to evaluate the effect of the products such as methyl oleate (Sigma commercial product, 99% purity), of the methyl esters of avocado and of a *Serenoa Repens* extract chosen as reference on the 5α-reductase activity. An in vitro model of normal human dermal fibroblast cultures was selected.

1. Materials and Methods 1.1 Test Products, Reference Product, and Reagents

The test products were provided by EXPANSCIENCE and were stored at +4° C. until the time of their use.

The radioactive testosterone (labeled with tritium at the 1, 2, 6 and 7 position, specific activity 79 Ci/mmol) was provided by AMERSHAM, the nonradiolabeled testosterone was provided by SIGMA.

The reagents of analytical grade, were obtained from SIGMA, MERCK, BDH, ALDRICH or CARLO ERBA unless otherwise stated.

1.2 Assay System

The fibroblast culture medium (FCM) consisted of MEM/M199 (3:1, v/v) supplemented with penicillin (50 IU/ml), streptomycin (50 µg/ml), sodium bicarbonate (0.2%, w/v) and FCS (10%, v/v).

The assay system consisted of normal human dermal fibroblasts cultured as a monolayer. The fibroblasts were isolated from a residue from abdominal plastic surgery performed on a 51 year old female (subject BIOPREDIC No. I0013). The cells were used at the fifth passage; they were cultured until the monolayers were confluent in FCM medium at 37° C. in a humid atmosphere containing 5% $CO_2$.

1.3 Preparation of the Products and Incubation with the Assay System

The fibroblast incubation medium (FIM) consisted of FCM supplemented with tritiated testosterone ($1.6 \times 10^{-7}$ M, that is 6.32 µCi/ml) and nonradiolabeled testosterone ($3.84 \times 10^{-6}$ M)

The test products and finasteride were taken up in DMSO before being diluted in the incubation medium. The final concentration of DMSO was kept constant and equal to 1% (v/v) in each dilution of test products and reference products.

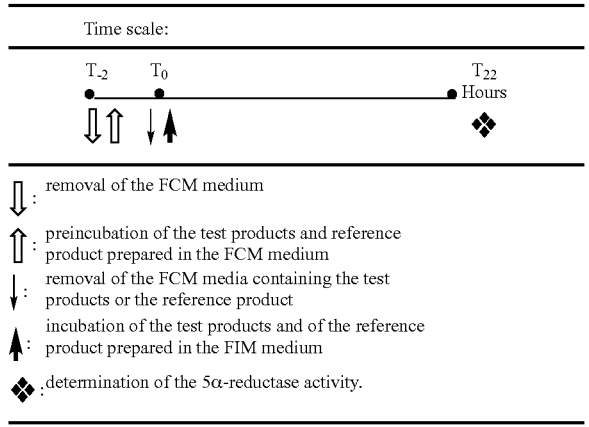

Time scale:

T₋₂    T₀           T₂₂ Hours

⇓ : removal of the FCM medium

⇑ : preincubation of the test products and reference product prepared in the FCM medium ↓ : removal of the FCM media containing the test products or the reference product ↑ : incubation of the test products and of the reference product prepared in the FIM medium ❖ : determination of the 5α-reductase activity.

The fibroblast cultures were preincubated in the presence of the test products or of the reference product for 2 hours before adding the substrate, testosterone. For this step, the test products and the reference product were prepared in the FCM medium.

After preincubation, the fibroblast cultures were incubated in the presence of the test products or of the reference product prepared in the FIM medium for 22 hours at 37° C. in a humid atmosphere containing 5% $CO_2$. Control cultures were incubated in the FIM medium in the absence of test products and of reference product. "DMSO control" cultures were incubated in the FIM medium containing 1% (v/v) of DMSO.

Each experimental condition was tested in triplicate.

1.4 Evaluation of the Effects

After the incubation period, the cells were subjected to the action of ultrasound in the FIM medium. The cellular lysates thus obtained were extracted with dichloromethane. After evaporation, the dry residues were taken up in methanol and were deposited on $60F_{254}$ silica plates (MERCK, reference 5554).

Nonradiolabeled standards, testosterone, 5α-dihydro-testosterone and androstenedione, were deposited on each of the plates.

The migration solvent was a mixture of dichloromethane and ether (7:3, v/v) At the end of the migration, the silica plates were read using a BERTHOLD radioactivity scanner.

The nonradiolabeled standards were visualized by spraying 5% sulfuric acid (v/v) over the chromatography plates which were then heated at 100° C. for 10 minutes.

Comparison of the Rf values (relative retardation factor) determined for the standards with those obtained for the various radioactive metabolites allowed the identification of the latter.

The metabolizing of testosterone to 5α-dihydro-testosterone under the various experimental conditions was calculated: the results (areas of the 5α-dihydrotestosterone peaks counted by the BERTHOLD scanner) were expressed in pmol of 5α-dihydro-testosterone formed per culture well. They were also expressed as a percentage of the 5α-reductase activity present in the "DMSO control" group.

1.5—Treatment of the Data

The groups of data (control group and treated groups) were treated by a one-way analysis of variance (ANOVA 1, p<0.05), followed by a DUNNETT's test (p<0.05). The effect of the test products and of the reference product was compared with the "DMSO control" group. The effects of the test products were compared to each other by a two-way analysis of variance (ANOVA 2, p<0.05, factor 1=concentration and factor 2=treatment).

2. Results and Discussion

In the control cultures, the rate of testosterone metabolism was 9.71+/−0.77 pmol of 5α-DHT formed in 22 hours per culture well. This rate was in conformity with the results already obtained in the laboratory.

The methyl esters of avocado, tested at 10 and 100 µg/ml, inhibited the 5α-reductase activity by 29 and 55% respectively (table 6).

The purified methyl oleate, tested at 1, 10 and 100 µg/ml, inhibited the 5α-reductase activity by 24, 38 and 41% respectively (table 7).

The *Serenoa Repens* extract, reference product, tested at 10 and 100 µg/ml, inhibited the 5α-reductase activity by 15 and 35% respectively. At 1 µg/ml, it had no effect (table 7).

In conclusion, the products tested inhibited the 5α-reductase activity.

Depending on the activity of the test products, tested at 10 and 100 µg/ml, the methyl esters of avocado and the purified methyl oleate exhibited a 5α-reductase inhibitory activity significantly higher than that of the *Serenoa repens* extract, chosen as reference.

This test therefore confirms the inhibitory activity of the methyl esters of fatty acids, and in particular those of avocado oil.

3. Tables 3.1—Effect of the Methyl Esters of Avocado on the 5α-Reductase Activity in Normal Human Dermal Fibroblast Cultures After 22 Hours of Incubation

TABLE 6

| Product | DMSO 1% (v/v) | Concentration (µg/ml) | |
|---|---|---|---|
| | | 10 | 100 |
| Methyl esters of avocado | 8.00 | 5.80 | 4.28 |
| | 8.92 | 6.36 | 2.72 |
| | 8.68 | 6.08 | 4.48 |
| | 8.53 +/− 0.48 | **6.08* +/− 0.28** | **3.83* +/− 0.96** |
| | *100* | *71* | *45* |

The results are expressed in pmol of 5α-DHT formed/culture well.
In bold: mean and standard deviation
In italics: percentage of the DMSO group
*: mean significantly different from the DMSO group (p < 0.05)

3.2—Effect of Methyl Oleate and of the *Serenoa Repens* Extract on the 5α-Reductase Activity in Normal Human Dermal Fibroblast Cultures after 22 Hours of Incubation.

TABLE 7

| Product | DMSO 1% (v/v) | Concentration (µg/ml) | | |
|---|---|---|---|---|
| | | 1 | 10 | 100 |
| Methyl oleate | 8.00 | 7.12 | 3.00 | 5.44 |
| | 8.92 | 6.24 | 7.04 | 5.12 |
| | 8.68 | 6.08 | 5.92 | 4.60 |
| | 8.53+/− 0.48 | **6.48*+/− 0.56** | **5.32*+/− 2.09** | **5.05*+/− 0.42** |
| | *100* | *76* | *62* | *59* |
| *Serenoa Repens* extract | 8.00 | 7.72 | 6.84 | 5.48 |
| | 8.92 | 9.20 | 7.48 | 5.68 |
| | 8.68 | 8.08 | 7.52 | 5.44 |
| | 8.53+/− 0.48 | 8.33 +/− 0.77 | **7.28*+/− 0.38** | **5.53*+/− 0.13** |
| | *100* | *98* | *85* | *65* |

The results are expressed in pmol of 5α-DHT formed/culture well.
In bold: mean and standard deviation
*: mean significantly different from the DMSO group (p < 0.05)

EXAMPLE 4

Evaluation in vitro of Fatty Acid Esters on the 5α-Reductase Activity for the Conversion of Testosterone to 5α-Dihydrotestosterone in Normal Human Dermal Fibroblast Cultures 1. Materials and Methods The same materials and methods are used as in example 3 above.

2—Results and Discussion

It was proposed to evaluate the effect of fatty acid esters on the 5α-reductase activity. An in vitro model of normal human dermal fibroblast cultures was selected. The products tested were chosen from the group of fatty acid esters varying in the length and the functionality of the fatty chain, and the nature of the alkoxy group. These esters are the following: methyl oleate, methyl linoleate, methyl stearate, methyl laurate, methyl undecylenate, butyl oleate, oleyl oleate and methyl ricinoleate.

Methyl oleate, tested at 1, 10 and 100 µg/ml, significantly inhibited (p<0.05) the 5α-reductase activity by 29%, 42% and 26% respectively.

Oleyl oleate, tested at 1, 10 and 100 µg/ml, significantly inhibited (p<0.05) the 5α-reductase activity by 28%, 45% and 35% respectively. At 10 and 100 µg/ml, the fibroblasts exhibited cellular suffering observed by morphological examination of the cells.

Butyl oleate, tested at 1, 10 and 100 µg/ml, significantly inhibited (p<0.05) the 5α-reductase activity by 21%, 45% and 49% respectively.

Methyl undecylenate, tested at 1, 10 and 100 µg/ml, significantly inhibited (p<0.05) the 5α-reductase activity by 40%, 32% and 26% respectively.

Methyl stearate, tested at 1, 10 and 100 µg/ml, significantly inhibited (p<0.05) the 5α-reductase activity by 41%, 35% and 43% respectively.

Methyl linoleate, tested at 1, 10 and 100 µg/ml, significantly inhibited (p<0.05) the 5α-reductase activity by 42%, 40% and 29% respectively.

Methyl ricinoleate, tested at 1, 10 and 100 µg/ml, significantly inhibited (p<0.05) the 5α-reductase activity by 37%, 38% and 62% respectively.

In conclusion, under the experimental conditions selected, depending on the activity of the test products, tested at 1, 10 and 100 µg/ml, it was possible to classify the test products into three groups:

Methyl oleate, butyl oleate, oleyl oleate and methyl ricinoleate=group A with the highest inhibitory activity. Methyl linoleate, stearate, laurate and undecylenate=group B with an intermediate inhibitory activity.

The products of group A exhibited a 5α-reductase inhibitory activity significantly (p<0.05) greater than that of the products of group B.

Within the group, the products had a comparable inhibitory activity.

2—Detailed Tables of Results: Effect of Fatty Acid Esters the 5α-Reductase Activity in Normal Human Dermal Fibrolast Cultures, after 24 of Incubation

TABLE 8

| Product | DMSO 0.1% (v/v) | Concentration (µg/ml) | | |
|---|---|---|---|---|
| | | 1 | 10 | 100 |
| Methyl oleate | 10.56 | 8.24 | 6.28 | 7.52 |
| | 12.00 | 8.28 | 6.44 | 7.00 |
| | 11.64 | 7.84 | 7.12 | 7.20 |
| | 11.40 +/− 0.75 | **8.12* +/− 0.24** | **6.61* +/− 0.45** | **7.24* +/− 0.26** |
| | *100* | *71* | *58* | *64* |
| Oleyl oleate | 10.56 | 9.00 | 6.12 | 6.28 |
| | 12.00 | 7.32 | 6.44 | 8.60 |
| | 11.64 | 8.20 | 6.20 | 7.48 |
| | 11.40 +/− 0.75 | **8.17* +/− 0.84** | **6.25* +/− 0.17** | **7.45* +/− 1.16** |
| | *100* | *72* | *55* | *65* |
| Butyl oleate | 10.56 | 10.64 | 6.24 | 5.20 |
| | 12.00 | 8.28 | 5.04 | 6.72 |
| | 11.64 | 8.08 | 7.36 | 5.40 |
| | 11.40 +/− 0.75 | **9.00* +/− 1.42** | **6.21* +/− 1.16** | **5.77* +/− 0.83** |
| | *100* | *79* | *55* | *51* |
| Methyl undecylenate | 10.56 | 6.56 | 7.68 | 8.68 |
| | 12.00 | 7.44 | 7.84 | 7.76 |
| | 11.64 | 6.68 | 7.60 | 9.00 |
| | 11.40 +/− 0.75 | **6.89* +/− 0.48** | **7.71* +/− 0.12** | **8.48* +/− 0.64** |
| | *100* | *60* | *68* | *74* |
| Methyl stearate | 10.56 | 6.92 | 8.80 | 6.88 |
| | 12.00 | 6.08 | 6.72 | 5.92 |

TABLE 8-continued

| Product | DMSO 0.1% (v/v) | Concentration (μg/ml) | | |
|---|---|---|---|---|
| | | 1 | 10 | 100 |
| | 11.64 | 7.08 | 6.76 | 6.76 |
| | 11.40 +/− | **6.69* +/−** | **7.43* +/−** | **6.52* +/−** |
| | 0.75 | 0.54 | 1.19 | 0.52 |
| | *100* | *59* | *65* | *57* |
| Methyl linoleate | 10.56 | 7.04 | 6.00 | 8.56 |
| | 12.00 | 6.40 | 6.60 | 8.04 |
| | 11.64 | 6.36 | 8.00 | 7.56 |
| | 11.40 +/− | **6.60* +/−** | **6.87* +/−** | **8.05* +/−** |
| | 0.75 | 0.38 | 1.03 | 0.50 |
| | *100* | *58* | *60* | *71* |
| Methyl ricinoleate | 10.56 | 6.52 | 7.84 | 3.68 |
| | 12.00 | 8.36 | 7.40 | 4.52 |
| | 11.64 | 6.68 | 5.88 | 4.80 |
| | 11.40 +/− | **7.19* +/−** | **7.04* +/−** | **4.33* +/−** |
| | 0.75 | 1.02 | 1.03 | 0.58 |
| | *100* | *63* | *62* | *38* |
| Methyl laurate | 10.56 | 5.76 | 6.84 | 8.48 |
| | 12.00 | 6.88 | 9.88 | 11.96 |
| | 11.64 | 6.84 | 9.52 | 8.96 |
| | 11.40 +/− | **6.49* +/− | 8.75 +/− | 9.80 +/−** |
| | 0.75 | 0.64 | 1.66 | 1.89 |
| | *100* | *57* | *77* | *86* |

The results are expressed in pmol of 5α-DHT formed/culture well.
In bold: mean and standard deviation
In italics: percentage of the "DMSO 0.1% (v/v)" group
Mean significantly different from the "DMSO 0.1% (v/v)" group

EXAMPLE 6

Composition of Hyperseborrhea Cream

| | % by weight |
|---|---|
| Butyl esters of avocado oil | 15.0 |
| Staryl alcohol | 3.0 |
| Steareth-21 | 3.0 |
| Steareth-2 | 2.0 |
| Water | qs 100 |
| Carbopol | 0.4 |
| Sodium hydroxide | 0.3 |
| Butylated hydroxytoluene (BHT) | 0.4 |
| Perfume | 0.1 |
| | 100% |

The invention claimed is:

1. A method of inhibiting 5 alpha reductase activity in a subject in need thereof, comprising
administering to said subject a composition comprising between 0.01 and 70% by weight of methyl oleate, methyl linoleate, methyl stearate, methyl laurate, methyl undecylenate, butyl oleate, oleyl oleate, methyl ricinoleate, butyl esters of avocado oil butyl esters of soybean oil, or a mixture thereof.

2. A method for inhibiting 5 alpha reductase activity, according to claim 1, wherein the composition comprises butyl esters of avocado oil, butyl esters of soybean oil, or a mixture thereof.

3. A method for inhibiting 5 alpha reductase activity, according to claim 1, wherein said composition comprises butyl oleate.

4. A method for inhibiting 5 alpha reductase activity, according to claim 1, wherein said composition comprises methyl ricinoleate.

5. A method for inhibiting 5 alpha reductase activity, according to claim 1, in which the composition prepared comprises a pharmaceutically, dermatologically or cosmetically acceptable excipient.

6. A method for inhibiting 5 alpha reductase activity, according to claim 5, in which the excipient is suitable for administration by the external topical route or by the rectal route.

7. A method for inhibiting 5 alpha reductase activity, according to claim 1, wherein the subject is suffering from prostatic hypertrophy.

8. A method for inhibiting 5 alpha reductase activity, according to claim 1, wherein the subject is suffering from prostatic adenoma.

9. A method for inhibiting 5 alpha reductase activity, according to claim 1, wherein the subject is suffering from acne.

10. A method for inhibiting 5 alpha reductase activity, according to claim 1, wherein the subject is suffering from hyperseborrhea.

11. A method for inhibiting 5 alpha reductase activity, according to claim 1, wherein the subject is suffering from alopecia.

12. A method for inhibiting 5 alpha reductase activity, according to claim 1, wherein the subject is suffering from hirsutism.

13. A method, according to claim 1, in which the composition is applied to the skin as a cosmetic treatment for greasy skin.

14. A method, according to claim 1, in which the composition is applied to the scalp as a cosmetic treatment for hair loss.

15. A method, according to claim 1, in which the composition is applied to the regions of the skin exhibiting excess pilosity as a cosmetic treatment for excess pilosity.

16. A method of cosmetic treatment, according to claim 13, in which the cosmetic composition contains, in addition, at least one cosmetically acceptable excipient.

17. A method of cosmetic treatment, according to claim 14, in which the cosmetic composition contains, in addition, at least one cosmetically acceptable excipient.

18. A method of cosmetic treatment, according to claim 15, in which the cosmetic composition contains, in addition, at least one cosmetically acceptable excipient.

19. A method for inhibiting 5 alpha reductase activity, according to claim 1, wherein the composition is an additive in a food product for a) human consumption, b) animal consumption, or c) a combination of a) and b).

20. A method for inhibiting 5 alpha reductase activity, according to claim 19, in which the fatty ester is present in the food in a proportion of between about 0.001 and about 100% by weight, relative to the total weight of the food.

21. A method for inhibiting 5 alpha reductase activity, according to claim 1, wherein said composition comprises methyl oleate, oleyl oleate, butyl oleate, methyl undecylenate, methyl stearate, methyl linoleate, methyl ricinoleate, or methyl laurate.

* * * * *